(12) United States Patent  (10) Patent No.: US 7,445,602 B2
Yamamori et al.  (45) Date of Patent: Nov. 4, 2008

(54) CARBON DIOXIDE SENSOR AND AIRWAY ADAPTER INCORPORATED IN THE SAME

(75) Inventors: Shinji Yamamori, Tokyo (JP); Yoshinobu Ono, Tokyo (JP); Fumihiko Takatori, Tokyo (JP); Hidetoshi Dainobu, Tokyo (JP); Masayuki Inoue, Tokyo (JP); Noriaki Todokoro, Tokyo (JP)

(73) Assignee: Nihon Kohden Corporation, Tokyo (JP)

( * ) Notice: Subject to any disclaimer, the term of this patent is extended or adjusted under 35 U.S.C. 154(b) by 0 days.

(21) Appl. No.: 11/476,768

(22) Filed: Jun. 29, 2006

(65) Prior Publication Data

US 2006/0247551 A1  Nov. 2, 2006

Related U.S. Application Data

(62) Division of application No. 10/779,852, filed on Feb. 18, 2004.

(30) Foreign Application Priority Data

Feb. 18, 2003  (JP) ............................ P2003-039775
Mar. 3, 2003  (JP) ............................ P2003-055349
May 26, 2003  (JP) ............................ P2003-147890

(51) Int. Cl.
*A61B 5/08*  (2006.01)

(52) U.S. Cl. .................. 600/532; 600/529; 128/201.27; 128/207.18

(58) Field of Classification Search .................. 73/23.2; 600/532; 422/84; 128/202.22, 203.22, 204.11, 128/204.12, 204.22, 204.23, 205.23, 206.29
See application file for complete search history.

(56) References Cited

U.S. PATENT DOCUMENTS

| | | | |
|---|---|---|---|
| 5,046,491 A | 9/1991 | Derrick | |
| 5,099,836 A * | 3/1992 | Rowland et al. | ....... 128/204.23 |
| 5,335,656 A | 8/1994 | Bowe et al. | |
| 5,572,994 A | 11/1996 | Smith | |
| 5,682,881 A | 11/1997 | Winthrop et al. | |
| 5,752,511 A | 5/1998 | Simmons et al. | |
| 6,155,986 A | 12/2000 | Brydon et al. | |
| 6,379,312 B2 | 4/2002 | O'Toole | |
| 6,422,240 B1 | 7/2002 | Levitsky et al. | |
| 6,726,637 B2 * | 4/2004 | Phillips | ...................... 600/543 |
| 6,938,619 B1 * | 9/2005 | Hickle | .................... 128/207.18 |
| 2001/0031929 A1 * | 10/2001 | O'Toole | ...................... 600/532 |
| 2002/0055685 A1 * | 5/2002 | Levitsky et al. | ............. 600/543 |
| 2002/0122746 A1 | 9/2002 | Yamamori et al. | |
| 2003/0199780 A1 * | 10/2003 | Page | ......................... 600/538 |

* cited by examiner

*Primary Examiner*—Charles A. Marmor, II
*Assistant Examiner*—Karen E Toth
(74) *Attorney, Agent, or Firm*—Sughrue Mion, PLLC

(57) ABSTRACT

In a sensor for detecting a carbon dioxide gas in an expiration gas of a living body, an airway case is adapted to be disposed below nostrils of the living body, and formed with an airway passage extending across an optical axis of a light beam emitted from a light emitter of the sensor. A mouth guide is adapted to be disposed in front of a mouth of the living body so as to define a space communicated with the airway passage. The mouth guide is pivotably supported on the airway case. A retainer is adapted to retain an oxygen supply tube on the airway adapter body in such an attitude that an oxygen gas supplied from prongs of the oxygen supply tube is not directly injected into the nostrils.

16 Claims, 16 Drawing Sheets

CARBON DIOXIDE SENSOR AND AIRWAY ADAPTER INCORPORATED IN THE SAME

This is a divisional of application Ser. No. 10/779,852 filed Feb. 18, 2004. The entire disclosure of the prior application, application Ser. No. 10/779,852 is hereby incorporated by reference.

BACKGROUND OF THE INVENTION

The present invention relates to a carbon dioxide sensor for measuring concentration, partial pressure, or presence/absence of carbon dioxide in a gas expired through nostrils or a mouth of a living body.

In general, when the concentration of carbon dioxide contained in an expiration gas expired from a living body is optically measured, the gas is led through a cylindrical airway adapter. An infrared ray is radiated onto the expired gas from a light-emitting element. The amount of light that remains after some of the light has been absorbed by the carbon dioxide contained in the expiration gas is detected by a light-receiving element, thus measuring the concentration of carbon dioxide.

FIG. 16 shows such an apparatus for measuring the concentration of carbon dioxide. In this apparatus, one end 101a of an airway adapter 101, which is formed into a substantially cylindrical shape and through which a respiration gas passes, is to be connected to a tube inserted into a trachea of a patient. Another end 101b is to be connected to a Y piece of a respiratory circuit, such as a respirator. An intermediate portion of the airway adapter 101 has a rectangular cross-sectional shape. Circular windows 101c, 101d are formed in respective, opposing surfaces of the intermediate portion such that the windows are concentrically aligned with each other.

A sensor body 102 is formed into a substantially-rectangular shape, and a notch is formed in an intermediate portion of the sensor body 102. The intermediate portion of the airway adapter 101 is to be detachably fitted with the notch. Two opposing surfaces defining the notch are in contact with the windows 101c, 101d of the airway adapter 101. A light-emitting element 103 is disposed on one side with reference to the notch.

An optical filter 104 for absorbing only light having a wavelength to be absorbed by carbon dioxide and a light-receiving element 105 are disposed on the side opposite the light-emitting element 103 with reference to the notch. The light-emitting element 103 and the light-receiving element 105 are connected to a monitor 107 via a lead wire 106.

In the apparatus having the foregoing configuration, the light emitted from the light-emitting element 103 enters the light-receiving element 105 by way of the window 101c, the respiration gas in the airway adapter 101, the window 101d, and the filter 104. The light-receiving element 105 detects the amount of light after some amount of the light has been reduced in accordance with the concentration of carbon dioxide. A signal output from the light-receiving element 105 is input to the monitor 107, where the concentration of carbon dioxide is displayed.

Another known apparatus has a structure in which a sampling tube is connected to a sensor body disposed in a monitor.

In such an apparatus, one end of the sampling tube which introduces a portion of a respiration gas is connected to an airway adapter through which the respiration gas passes. The other end of the sampling tube is connected to the monitor. A pump is disposed in the monitor to lead the introduced respiration gas to the sensor body disposed in the monitor.

Moreover, as shown in FIG. 17, an apparatus capable of measuring the concentration of carbon dioxide in an oral expiration gas as well as the concentration of carbon dioxide in a nasal expiration gas is known (see, e.g., U.S. Pat. No. 5,046,491).

This apparatus is provided with a respiration gas collector 110 having: a nasal cannula 111 for collecting a nasal respiration gas; an outwardly-convex mouth guide 113 for collecting an oral respiration gas; an oral respiration gas collector 114 which is disposed in the mouth guide 113 and collects an oral respiration gas; and a joint stem 112 which is connected at one end thereof to an external upper portion of the mouth guide 113 and at the other end thereof to the nasal cannula 111.

However, the respiration gas collector 110 involves a large number of components, because the joint stem 112 is constituted of separate members. Further, the joint stem 112 must be attached to two points; that is, the mouth guide 113 and the nasal cannula 111. This entails consumption of man-hours and, by extension, costs.

Further, in the respiration gas collector 110, the oral respiration gas collector 114 is disposed in the mouth guide 113 in order to cause a respiration gas to flow through an airway passage provided in the upper portion of the mouth guide 113. Hence, the oral respiration gas collector 114 exerts gas flow resistance, which inhibits efficient flow of the oral expiration gas through the airway passage.

In a case where oxygen is also supplied in conjunction with collection of the respiration gas, an oxygen supply tube is also attached to the patient. In such a case, prongs are inserted into nostrils. Alternatively, even in a case where an oxygen supply tube which does not entail insertion of the prongs into the nostrils, the prongs are oriented so that oxygen supplied by way of the prongs is injected directly toward the nostrils, which induces a problem of abrupt drying of the nostrils, causing the patient discomfort.

SUMMARY OF THE INVENTION

It is therefore an object of the invention to provide an airway adapter for a carbon dioxide sensor in which an oral expiration gas can be efficiently supplied to an airway passage located at an upper portion of a mouth guide.

It is also an object of the invention to provide an airway adapter for a carbon dioxide sensor in which the position of the mouth guide can be adjusted in accordance with the contour or size of a patient's face.

It is also an object of the invention to provide an airway adapter for a carbon dioxide sensor in which the number of element and the manufacturing cost can be reduced.

It is also an object of the invention to provide an airway adapter for a carbon dioxide sensor in which oxygen supplied from prongs can be prevented from directly injecting into patient's nostrils, in order to avoid abrupt drying of the nostrils.

In order to achieve the above objects, according to the invention, there is provided an airway adapter of a sensor for detecting a carbon dioxide gas in an expiration gas of a living body, comprising:

an airway case, adapted to be disposed below nostrils of the living body, and formed with an airway passage extending across an optical axis of a light beam emitted from a light emitter of the sensor; and a mouth guide, adapted to be disposed in front of a mouth of the living body so as to define a space communicated with the airway passage, the mouth guide being pivotably supported on the airway case.

In such a configuration, the mouth guide can be disposed in the vicinity of the mouth in accordance with the contour or size of a face of the living body.

Further, since the space defined by the mouth guide is communicated with the airway passage, an oral expiration gas can be smoothly guided to the airway passage to be subjected to the carbon dioxide detection.

Preferably, a shaft member is integrally molded with the mouth guide, and fitted into a hole formed in the airway case, so that the mouth guide is pivoted about the hole. In such a configuration, the number of parts can be reduced.

Here, it is preferable that the shaft member is extending in a first direction substantially parallel with a face of the living body, and the mouth guide is pivotable about the shaft member in a second direction perpendicular to the first direction.

Here, it is also preferable that the shaft member is formed with a flexible material so as to have a size which is no less than a size of the hole. In such a configuration, appropriate resistance is afforded when the mouth guide is pivoted.

It is also preferable that at least one of the airway case and the mouth guide is formed with an elastic material, so as to generate an elastic force directed in an extending direction of the shaft member. In such a configuration, appropriate resistance is afforded when the mouth guide is pivoted.

According to the invention, there is also provided an airway adapter of a sensor for detecting a carbon dioxide gas in an expiration gas of a living body, comprising:

an airway case, adapted to be disposed below nostrils of the living body, and formed with an airway passage extending across an optical axis of a light beam emitted from a light emitter of the sensor; and a retainer, adapted to retain an oxygen supply tube on the airway case in such an attitude that an oxygen gas supplied from prongs of the oxygen supply tube is not directly injected into the nostrils.

In such a configuration, an oxygen gas can be supplied during the detecting operation for the carbon dioxide gas. Further, since the supplied oxygen gas is not directly injected into the nostrils, abrupt drying of the nostrils can be avoided.

Preferably, the oxygen supply tube is retained at such a position that a gap is defined between the prongs and the nostrils.

Preferably, the airway adapter further comprises a mouth guide, adapted to be disposed in front of a mouth of the living body so as to define a space communicated with the airway passage, the mouth guide being pivotably supported on the airway case.

In such a configuration, the mouth guide can be disposed in the vicinity of the mouth in accordance with the contour or size of a face of the living body.

In any of the above airway adapters, it is preferable that the airway adapter further comprises an inlet member, adapted to be inserted into at least one of the nostrils having a passage for guiding a nasal expiration gas to the airway passage, the inlet member being formed with a vent hole communicating the passage and an exterior of the inlet member.

In such a configuration, the gas stayed in the airway passage can be smoothly escaped therefrom by the oral expiration gas with the aid of the vent hole. Further, even if the inlet member is clogged with a nasal mucus, the gas stayed in the airway passage is discharged to the exterior by way of the vent hole. Therefore, superior escape of the gas from the airway passage is achieved. Even when the amount of respiration is small, a sufficient amount of oral expiration gas for the detection can be introduced into the airway passage.

Here, it is further preferable that the passage of the inlet member is defined by a pair of tube members adapted to be inserted into the nostrils and a junction at which the tube members are merged. The vent hole is formed at the junction.

In such a configuration, when the oral expiration gas is guided to the airway passage, the gas remaining in the airway passage is discharged to the exterior by way of the pair of tube members and the vent hole. Even if the tube members are clogged with a nasal discharge, the gas in the airway passage is discharged to the exterior. Consequently, superior escape of the gas from the airway passage is achieved. Even when the amount of respiration is small, a sufficient amount of oral expiration gas for the detection can be introduced into the airway passage.

It is also preferable that the vent hole is arranged such that a flow of a gas discharged from the vent hole is not substantially interfered by the living body.

It is also preferable that the vent hole is arranged so as not to oppose to a face of the living body.

In such configurations, when the oral expiration gas is guided to the airway passage, the gas remaining in the airway passage can be efficiently discharged to the exterior while being less likely to be impeded by the living body. Even when the amount of respiration is small, a sufficient amount of oral expiration gas for detection can be introduced into the airway passage.

According to the invention, there is also provided a sensor for detecting a carbon dioxide gas in an expiration gas of a living body, comprising:

a photo emitter;

a photo receiver; and an airway adapter, which supports the photo emitter and the photo receiver such that a light beam emitted from the photo emitter is received by the photo receiver, the airway adapter comprising:

an airway case, adapted to be disposed below nostrils of the living body, and formed with an airway passage extending across an optical axis of the light beam; and a mouth guide, adapted to be disposed in front of a mouth of the living body so as to define a space communicated with the airway passage, the mouth guide being pivotably supported on the airway case.

According to the invention, there is also provided a sensor for detecting a carbon dioxide gas in an expiration gas of a living body, comprising:

a photo emitter;

a photo receiver; and an airway adapter, which supports the photo emitter and the photo receiver such that a light beam emitted from the photo emitter is received by the photo receiver, the airway adapter comprising:

an airway case, adapted to be disposed below nostrils of the living body, and formed with an airway passage extending across an optical axis of the light beam; and a retainer, adapted to retain an oxygen supply tube on the airway case in such an attitude that an oxygen gas supplied from prongs of the oxygen supply tube is not directly injected into the nostrils.

According to the invention, there is also provided a sensor for detecting a carbon dioxide gas in an expiration gas of a living body, comprising:

a photo emitter;

a photo receiver;

an oxygen supply tube;

an airway adapter, which supports the photo emitter and the photo receiver such that a light beam emitted from the photo emitter is received by the photo receiver, the airway adapter comprising:

an airway case, adapted to be disposed below nostrils of the living body, and formed with an airway passage extending across an optical axis of the light beam; and a retainer, which retains the oxygen supply tube on the airway case in such an attitude that an oxygen gas supplied from prongs of the oxygen supply tube is not directly injected into the nostrils.

BRIEF DESCRIPTION OF THE DRAWINGS

The above objects and advantages of the present invention will become more apparent by describing in detail preferred exemplary embodiments thereof with reference to the accompanying drawings, wherein.

DETAILED DESCRIPTION OF THE INVENTION

Embodiments of the present invention will be described below in detail with reference to the accompanying drawings.

Figure 1:
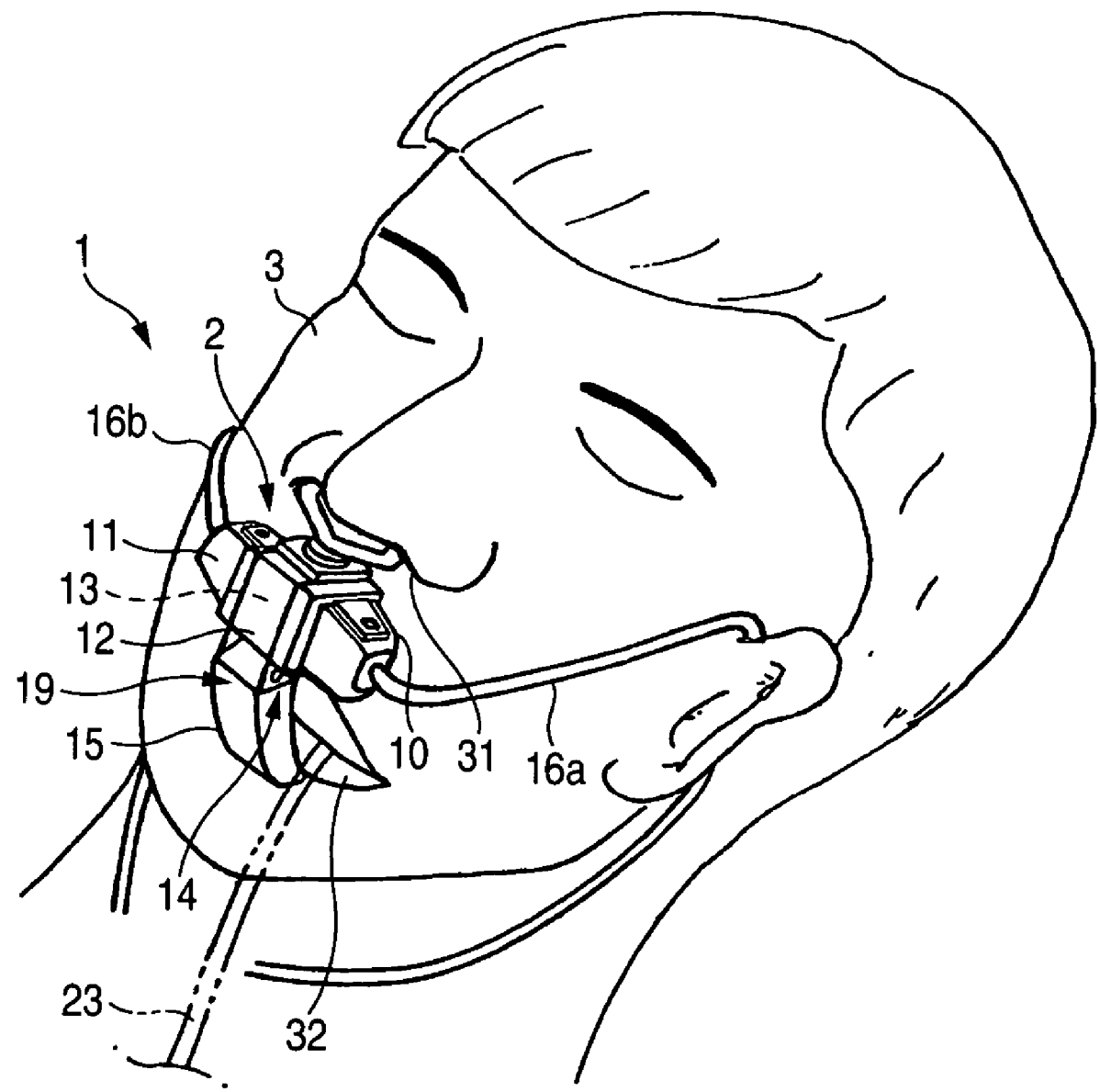
FIG. 1 is a perspective view of a carbon dioxide sensor according to a first embodiment of the invention, showing a state that the sensor is attached to a patient.

FIG. 1 shows a carbon dioxide sensor 1 according to a first embodiment of the present invention. In order to measure the concentration, partial pressure, or presence/absence of a carbon dioxide in an expired gas of a patient (living body) 3, the carbon dioxide sensor 1 comprises a light-emitting element 10 and a light-receiving element 11, which are arranged so as to oppose to each other on an optical axis thereof; a lead wire 16a for transmitting a light emission signal from the unillustrated carbon dioxide measurement apparatus to the light-emitting element 10; and a lead wire 16b for transmitting a light detection signal from the light-receiving element 11 to the carbon dioxide measurement apparatus; and an airway adapter 2.

The airway adapter 2 comprises: an airway case 12 for supporting the light-emitting element 10 and the light-receiving element 11; and an airway passage 13 (see FIG. 2) which enables a respiration gas of the patient 3 to pass through the optical axis when the airway case 12 is attached to an area located below nostrils 31 of the patient 3; a horizontal shaft 14 which is disposed on a wall portion 19 extending downward from the airway case 12 so as to be parallel to the surface of the face of the patient 3; a mouth guide 15 which is pivotable about the horizontal shaft 14 to approach or depart from a mouth 32 of the patient 3 with appropriate pivotal resistance; and a flexible tube (nasal tube) 21 (see FIG. 3).

Figure 2:
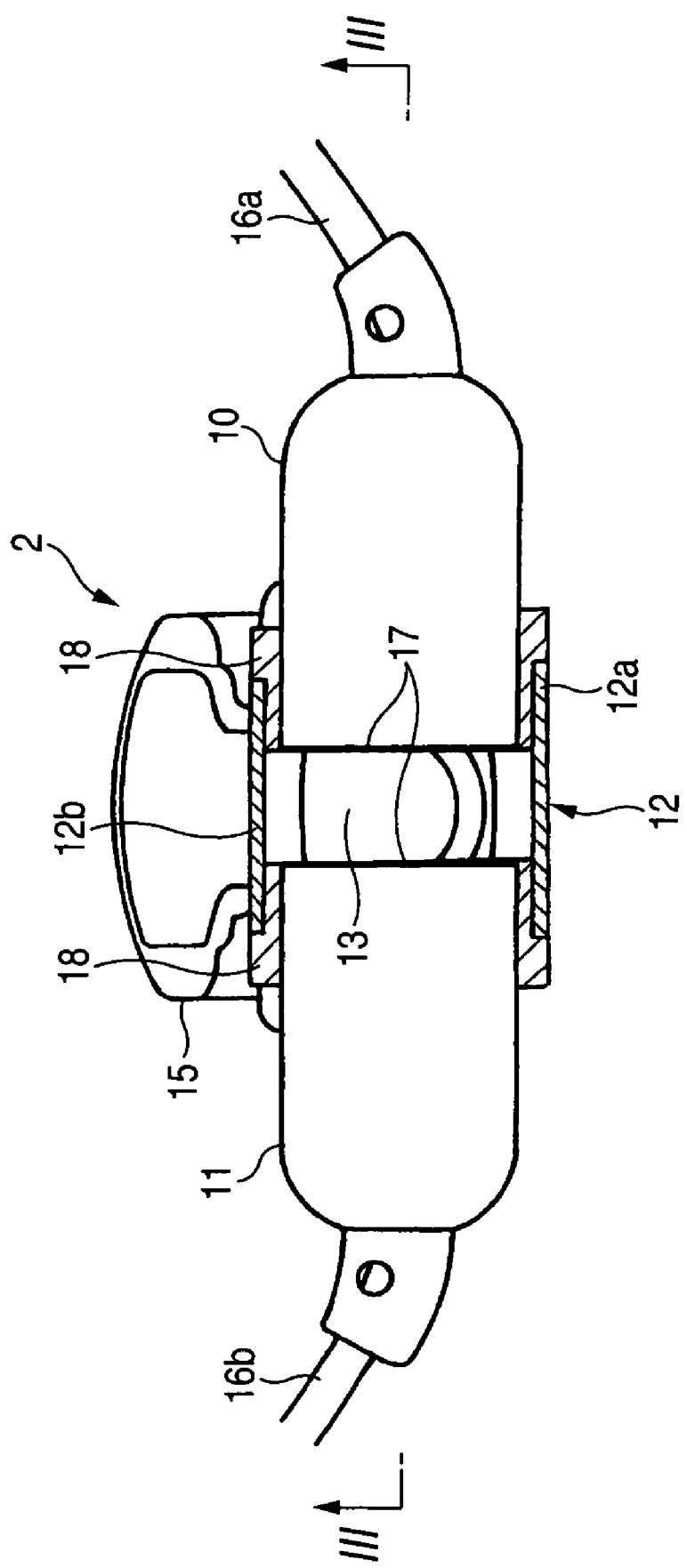
FIG. 2 is a cross-sectional view of an airway case in the sensor of the first embodiment.

The airway case 12 is formed from nonflexible resin. As shown in FIG. 2, the light-emitting element 10 and the light-receiving element 11 are hermetically sealed within the airway case 12 by anti-fogging films 17 whose mutually-opposing surfaces permit transmission of light and prevent fogging which would otherwise be caused by the respiration gas.

The airway passage 13 is defined by interior walls 12a, 12b and the anti-fogging films 17, both being provided in the airway case 12.

An optical filter (not shown) for permitting passage of only light having a wavelength to be absorbed by a carbon dioxide is disposed on the side of the light-receiving element 11. In FIG. 2, reference numeral 18 designates an anti-fogging film case.

The light-emitting element 10 is equipped with the lead wire 16a, and the light-receiving element 11 is equipped with the lead wire 16b.

Figure 3:
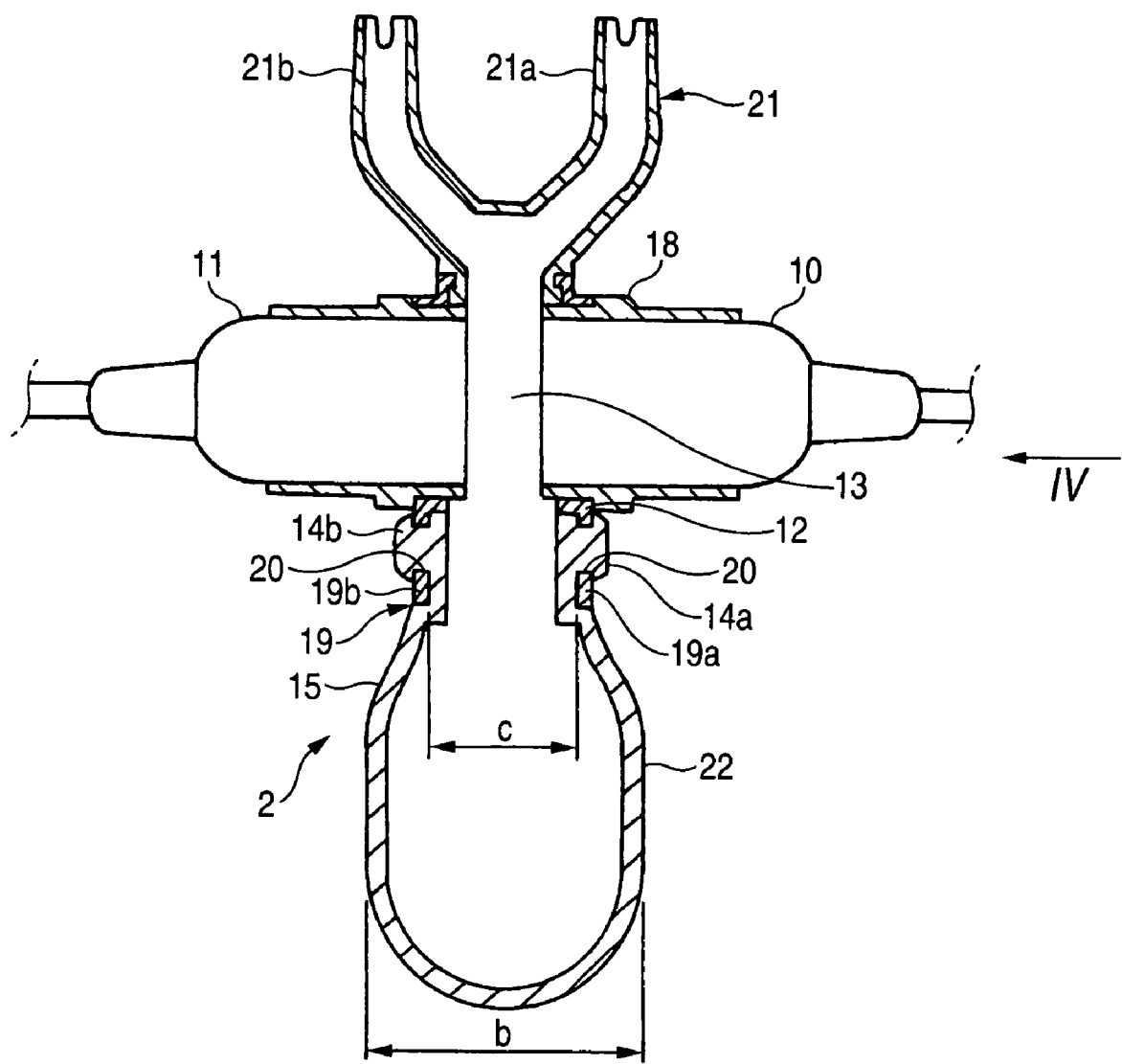
FIG. 3 is a cross-sectional view of the sensor taken along line III-III shown in FIG. 2.

As shown in FIG. 3, the airway passage 13 is connected to the flexible tube 21. This flexible tube 21 is formed from silicon rubber or the like or from vinyl chloride, polypropylene, polyethylene, an elastomer, or the like.

The flexible tube has a pair of inlets 21a, 21b. When the inlets 21a, 21b, which are Y-shaped, are inserted into the nostrils 31 of the patient 3 (see FIG. 1), a nasal expiration gas is guided to the airway passage 13 by way of the flexible tube 21.

In the side of the airway case 12 opposite to the side where the flexible tube 21 is attached, the mouth guide 15 is attached such that the respiration gas flows into the airway passage 13. The mouth guide 15 is formed from a soft material and is tongue-shaped when viewed from the front side thereof so as to have an appropriate width "b"; e.g., 20 mm or less.

The width "b" is preferably sufficiently narrow that a suction tube 23 (see FIG. 1) can be inserted into the mouth 32 while the patient 3 is wearing the carbon dioxide sensor 1, and sufficiently wide enough to receive the respiration gas from the mouth 32. To this end, the width "b" of the mouth guide 15 is preferably set to approximately 5 to 20 mm.

In order to minimize escape of the respiration gas, a sidewall 22 (see FIG. 4) is provided on both sides of the mouth guide 15 such that a concave space facing the mouth 32 is defined.

Figure 4:
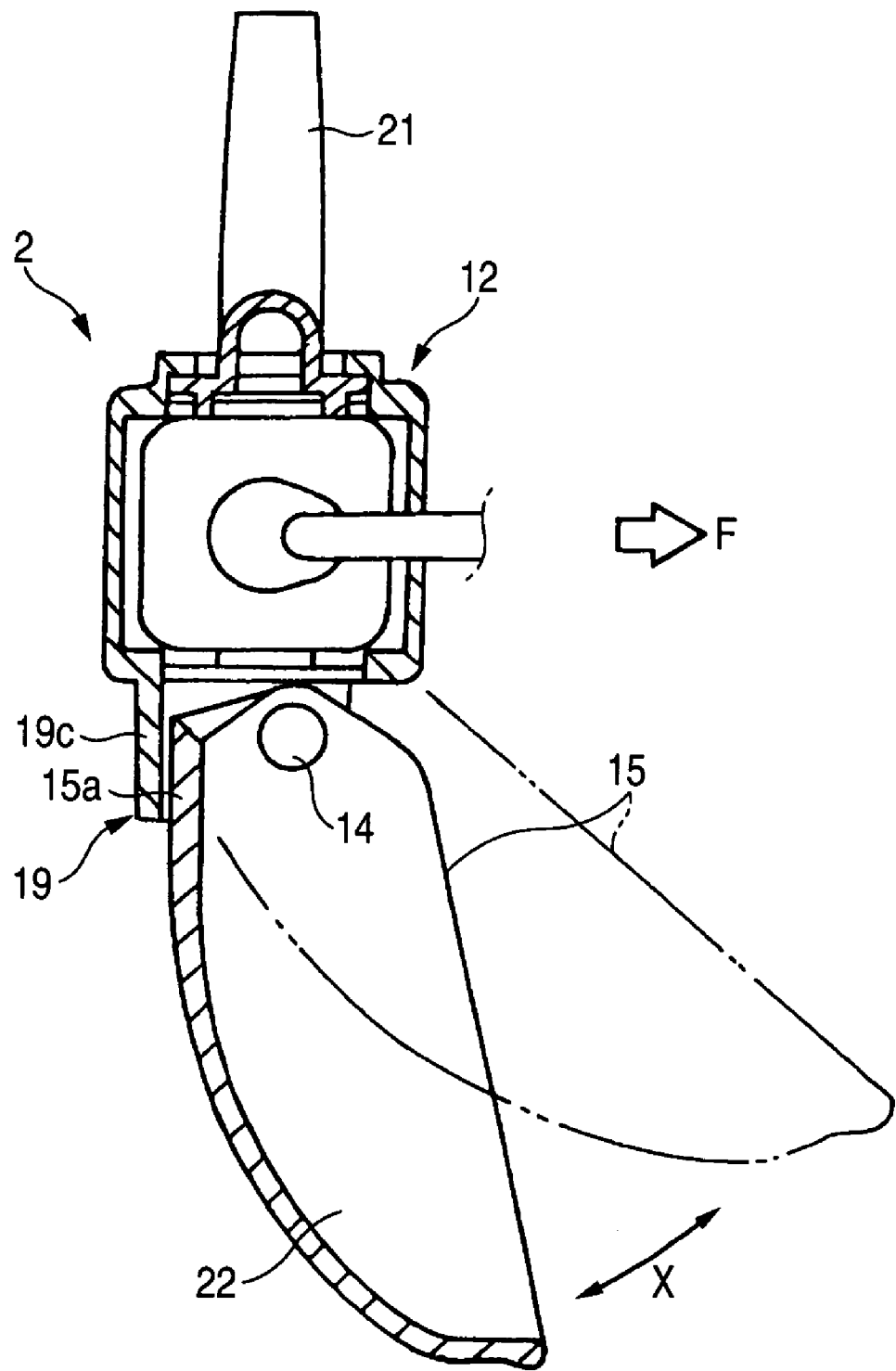
FIG. 4 is a view of the sensor when viewed in the direction of arrow IV shown in FIG. 3.

As shown in FIG. 4, the mouth guide 15 is configured so as to be pivotable about the horizontal shaft 14 latched by the wall portion 19 in a direction X in which the mouth guide 15 approaches and departs from the mouth 32 of the patient 3 (see FIG. 1); that is, in the forward and backward directions. The mouth guide 15 is attached to the sensor 1 such that the direction designated by arrow F is directed toward the face.

Material of the mouth guide 15 can be selected, as required, from soft materials such as vinyl chloride, polypropylene, polyethylene, silicon rubber, or an elastomer.

As shown in FIGS. 3 and 4, the wall portion 19 is constituted of continuous walls 19a, 19b, and 19c so as to define a space opened to the face of the patient 3. Holes 20 are coaxially formed in the opposing walls 19a and 19b so as to extend horizontally and parallel to the face of the patient 3.

As shown in FIG. 3, the horizontal shaft 14 is formed integrally from the mouth guide 15 and made up of mushroom-shaped shafts 14a, 14b having the same dimensions. The outer diameters of small-diameter sections of the respective shafts 14a, 14b are determined so as to be slightly larger than the diameters of holes 20 of the walls 19a, 19b, in a state before the shafts 14a, 14b are fitted into the holes 20. The shafts 14a, 14b are tightly fitted into the holes 20 so that the mouth guide 15 can pivot about the holes 20 (shafts 14a, 14b) with appropriate resistance.

A slit may be formed in each mushroom-shaped top of the shafts 14a, 14b to facilitate the insertion of the shafts 14a, 14b into the holes 20.

As shown in FIG. 4, the wall 19c of the wall portion 19 is configured so as to cover an end section 15a proximate to the horizontal shaft 14 of the mouth guide 15 even when the mouth guide 15 is situated a position close to the face of the patient 3 (i.e., a position indicated by a dashed chain line), thereby reducing a flow resistance against the expiration gas flowing from the mouth 32 into the airway passage 13.

The mouth guide 15 is pivotable about the horizontal shaft 14 back and forth with appropriate resistance. Therefore, even when the shape and size of the face of the patient 3 varies from that corresponding to the current configuration the mouth guide 15 is subjected to positional adjustment along the contour of the face and can be caused to approach the mouth 32 of the patient 3.

Therefore, the expiration gas from the mouth 32 of the patient 3 can be reliably led to the airway passage 13 of the airway case 12. As a result, the concentration of carbon dioxide in the oral expiration gas can be measured reliably.

Since the horizontal shaft 14 is formed integrally with the mouth guide 15, the mouth guide can be manufactured inexpensively. Therefore, the number of parts and the manufacturing cost can be reduced.

In the present embodiment, the shafts 14a, 14b are tightly fitted into the holes 20 to impart resistance to the pivotal movement of the mouth guide 15. Alternatively, the dimension "c" of the mouth guide 15 shown in FIG. 3 (i.e., a distance between proximal ends of the shafts 14a, 14b) may be made greater than the inner distance between the walls 19a, 19b before the shafts 14a, 14b are assembled into the holes 20. In such a case, a horizontal repulsion force develops in an area where the mouth guide 15 is in contact with the walls 19a, 19b, so that appropriate resistance can be imparted to the pivotal movement of the mouth guide 15.

In this case, in order to facilitate the assembling operation, the small diameters of the shafts 14a, 14b may be made smaller than the internal diameters of the holes 20, so that the shafts 14a, 14b may be respectively loosely fitted into the holes 20.

In order to further facilitate the assembling operation, in the above case, the shafts 14a, 14b may be merely shaped cylindrical to be loosely fitted into the holes 20.

In the loose-fitting configuration, the material of the mouth guide 15 may not be the soft material. However, it is necessary to configure the marginal shape of the mouth guide 15 so as not to inflict any pain on the living body even if the mouth guide 15 comes into contact with the living body.

In this embodiment, the horizontal shaft 14 is formed integrally with the mouth guide 15, and the holes 20 are formed in the wall portion 19 of the airway case 12. However, the horizontal shaft 14 may be formed integrally with the wall portion 19, and the holes 20 may be formed in the mouth guide 15.

In this case, so long as the mouth guide 15 is formed from a soft material, the horizontal shaft 14 made of unsoft resin can be readily inserted into the holes 20.

In this embodiment, the wall portion 19 is constituted of the three walls 19a, 19b, and 19c so as to have a rectangular horizontal cross section. However, the wall portion 19 may be configured so as to have a semi-circular or a semi-oval horizontal cross section, for example, only if the wall portion 19 defines a space opened to the face of the patient 3.

There will be described a second embodiment of the invention in which a hook 33 is provided in the carbon dioxide sensor 1 for retaining an oxygen supply tube (which may also be for general purpose use).

Figure 5:
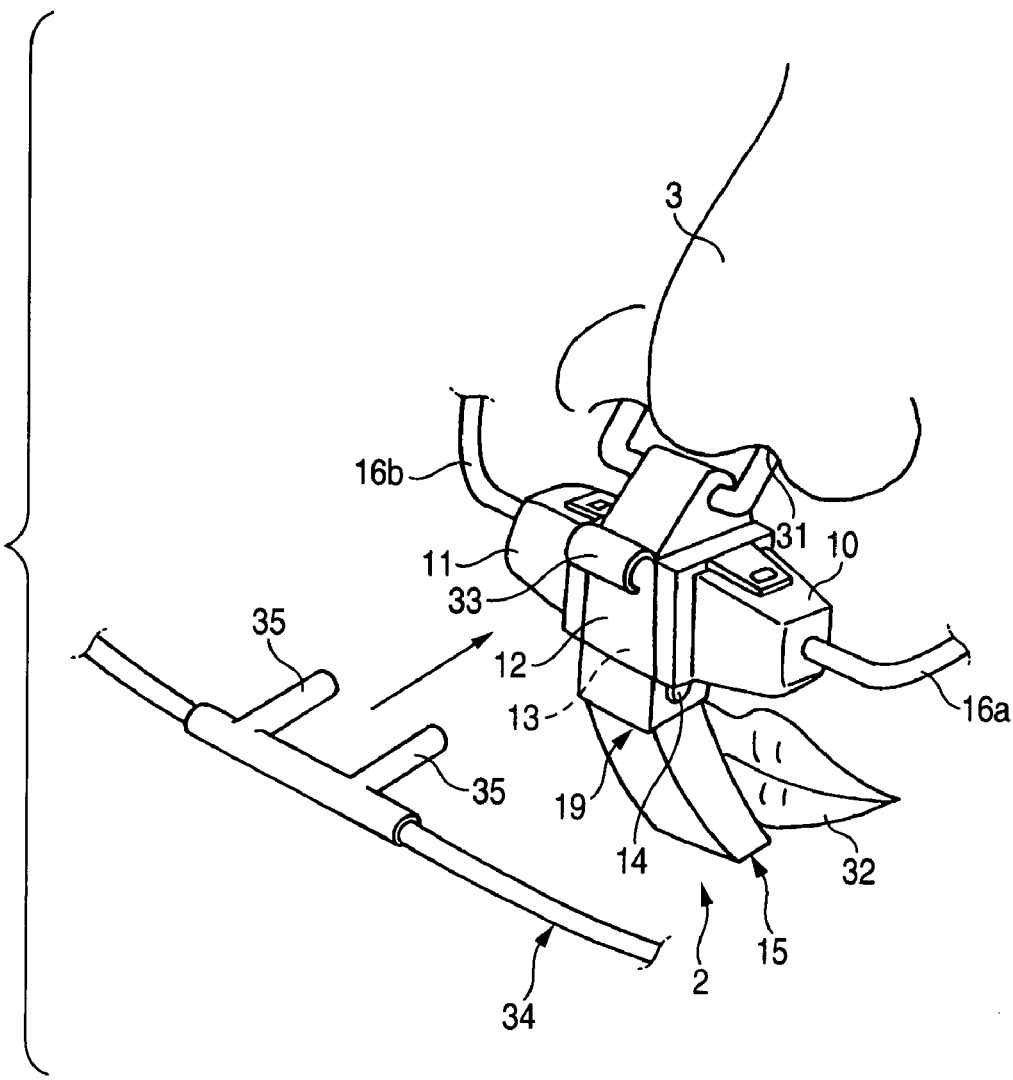
FIG. 5 is a fragmentary perspective view of a carbon dioxide sensor according to a second embodiment of the invention, showing a state that the sensor is attached to a patient.

As shown in FIG. 5, the hook 33 is provided on the back face of the airway case 12 of the carbon dioxide sensor 1 (i.e., the side opposite to the side facing the face of the patient 3 when the sensor is attached to the living body), to thereby enable attachment of an oxygen supply tube 34.

Figure 6:
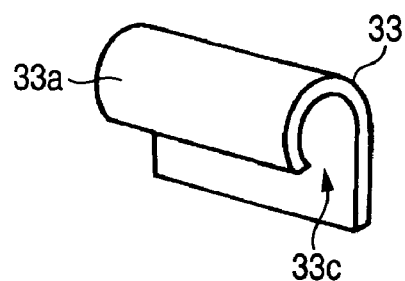
FIG. 6 is a fragmentary perspective view showing a hook in the sensor of the second embodiment.

As shown in FIG. 6, the hook 33 has a curved portion 33a defining an opened section 33c. A tube portion of the oxygen supply tube 34 located between two prongs 35 is attached to the hook 33 by way of the opened section 33c. In order to prevent deformation of the prongs 35, which would otherwise be caused by application of external force, the width of the curved portion 33a is preferably made equal to the distance between the two prongs 35. The curved portion 33a can be applied to the oxygen supply tube 34 regardless of the diameter thereof, through use of an elastic material. Such a hook 33 is bonded to the back face of the airway case 12.

Figure 7A:
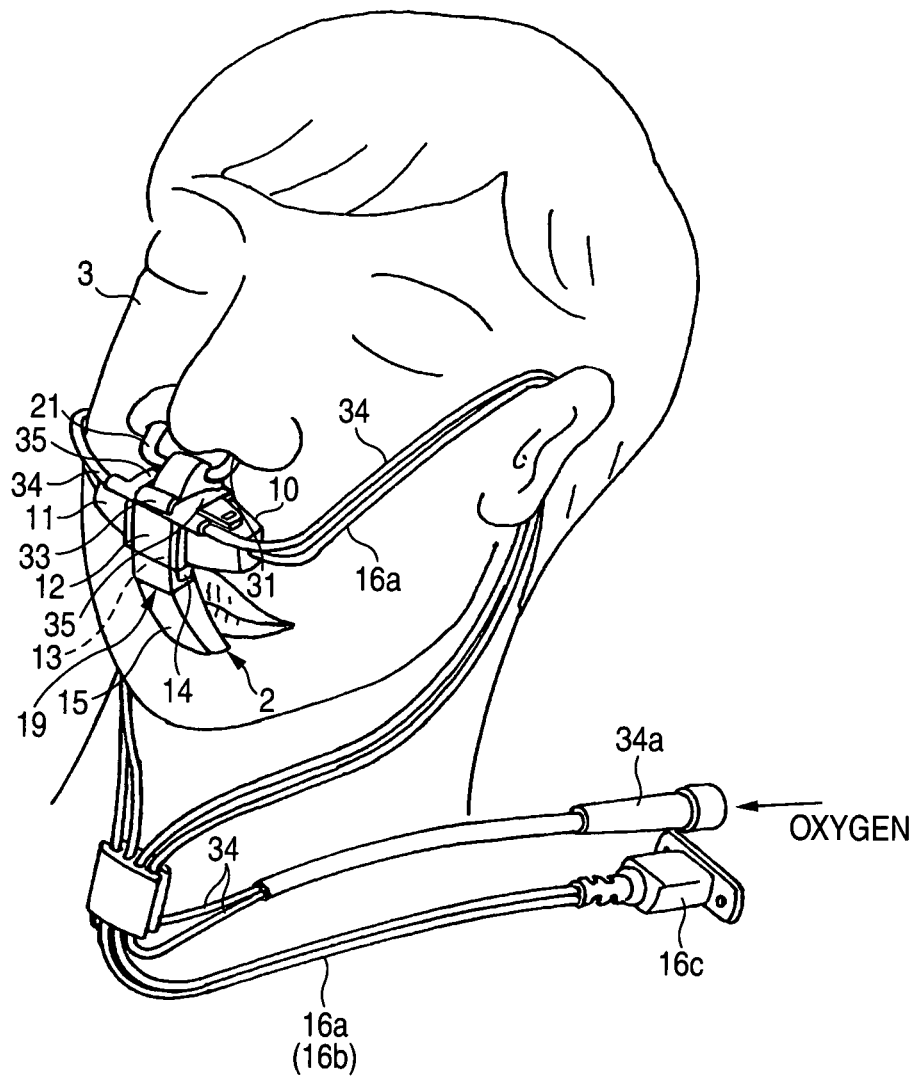
FIG. 7A is an overall perspective view showing the sensor of the second embodiment.
Figure 7B:
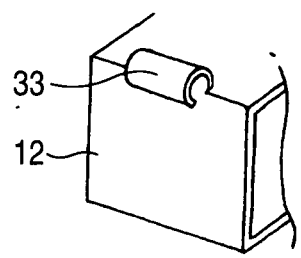
FIG. 7B is a fragmentary perspective view of a first modified example of the sensor of the second embodiment.

Alternatively, as a first modified example shown in FIG. 7B, the airway case 12 and the hook 33 may be formed integrally.

FIG. 7A is a view showing a state in which the hook 33 is used while the oxygen supply tube 34 is attached to the hook.

Reference numeral 34a designates an oxygen supply port of the oxygen supply tube 34. Reference numeral 16c designates a connector for electrically connecting an electric current employed for driving the light-emitting element 10 and the signal detected by the light-receiving element 11 to the not shown measurement apparatus.

Incidentally, the prongs 35 are made not to be inserted into the nostrils and arranged such that the oxygen supplied from the prongs 35 is not injected directly into the nostrils. As a result, abrupt drying of the nostrils can be prevented.

In the embodiment shown in FIG. 7A, in order to realize such an arrangement, the hook 33 is disposed such that the prongs 35 are arranged on a top face of the airway case 12. In this case, the oxygen supplied from the prongs 35 is not injected directly into the nostrils. The oxygen is aspirated by the nostrils after having come into collision with the skin located below the nose and wafted.

Figure 8A:
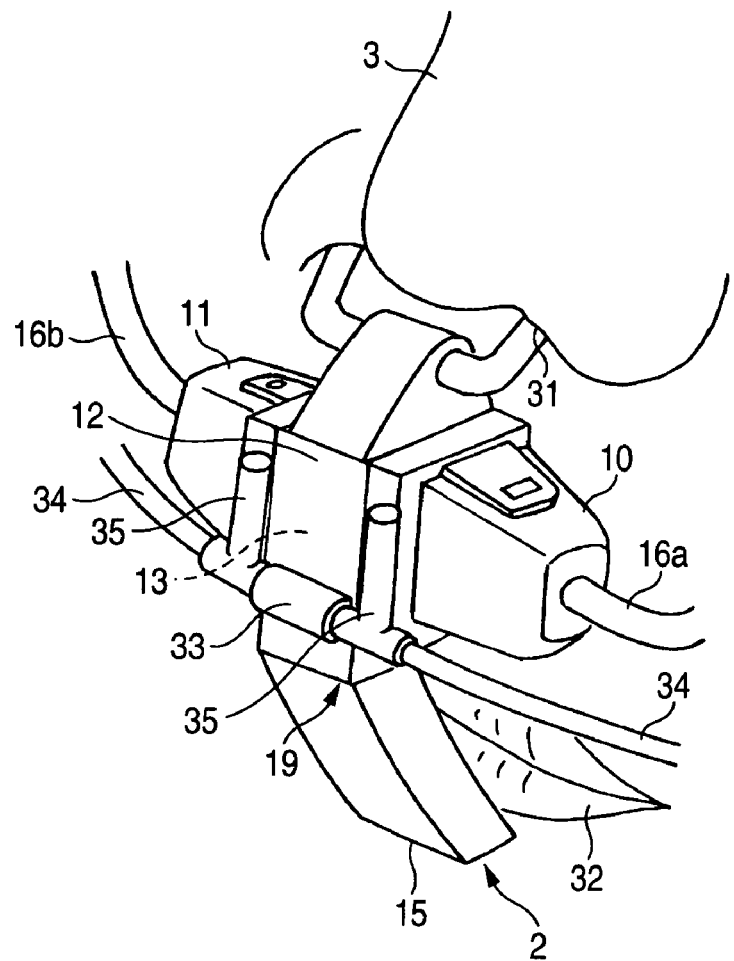
FIG. 8A is a fragmentary perspective view of a second modified example of the sensor of the second embodiment.

FIG. 8A shows a second modified example of this embodiment featuring a different arrangement of the hook 33. The hook 33 is provided such that the prongs 35 are aligned in line with the back of the airway case 12. In this case, the oxygen supplied from the prongs 35 is directed parallel to the back face of the airway case 12 toward the flexible tube 21 and wafted and aspirated by the nostrils.

Figure 8B:
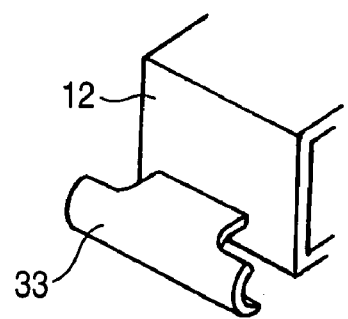
FIG. 8B is a fragmentary perspective view of a third modified example of the sensor of the second embodiment.

As a third modified example of this embodiment shown in FIG. 8B, the hook 33 may be formed integrally with the airway case 12.

Figure 9A:
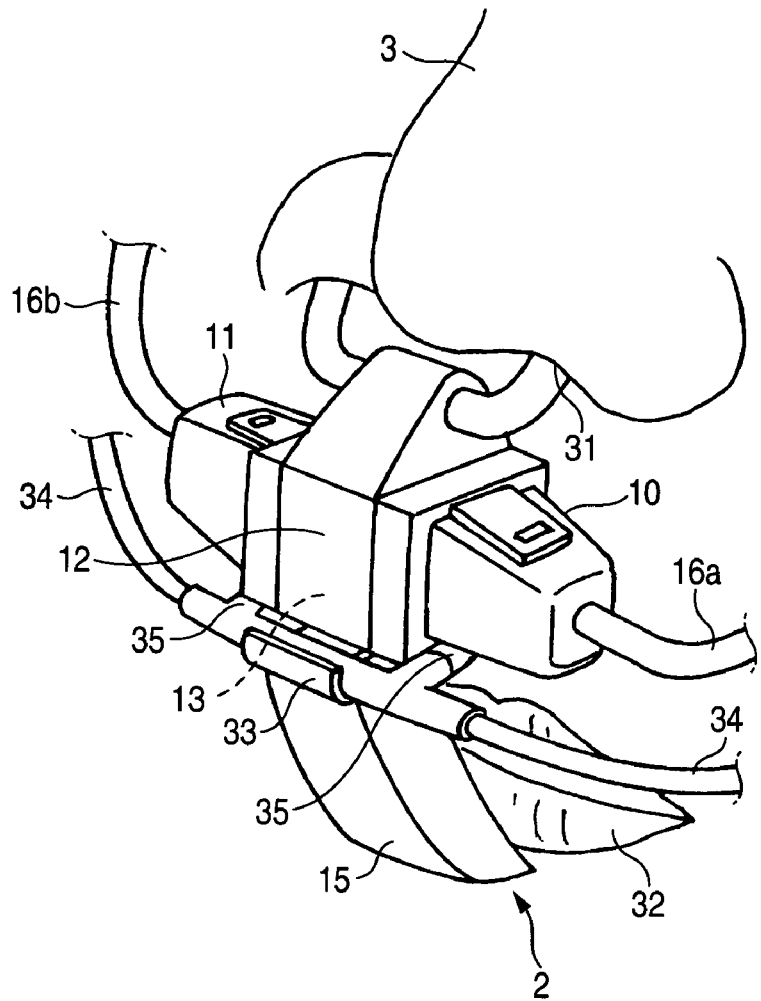
FIG. 9A is a fragmentary perspective view of a fourth modified example of the sensor of the second embodiment.

FIG. 9A shows a fourth modified example of this embodiment featuring a further different layout of the hook 33. The hook 33 is provided such that the prongs 33 are aligned with a bottom face of the airway case 12. Even in this case, as in the case shown in FIG. 7A, the oxygen supplied by way of the prongs 35 is not injected directly into the mouth and aspirated.

Figure 9B:
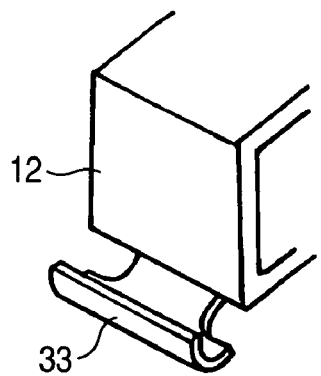
FIG. 9B is a fragmentary perspective view of a fifth modified example of the sensor of the second embodiment.

As a fifth modified example of this embodiment shown in FIG. 9B, the hook 33 may be formed integrally with the airway case 12.

Figure 10A:
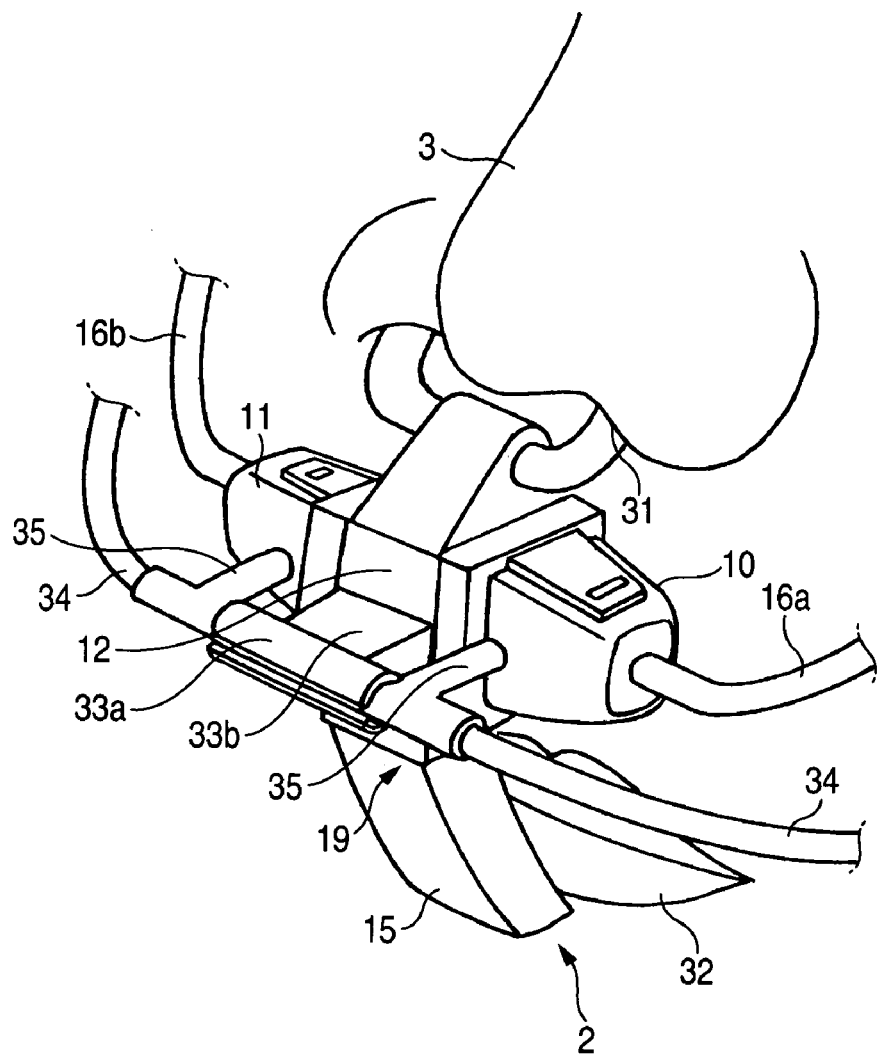
FIG. 10A is a fragmentary perspective view of a sixth modified example of the sensor of the second embodiment.

FIG. 10A shows a sixth modified example of this embodiment featuring a still further different layout of the hook 33. The hook 33 is disposed on the back face of the airway case 12 such that the extremities of the prongs 35 are directed toward the back face of the airway case 12 by rendering a handle 33b of the hook sufficiently long. By adoption of such a configuration, the oxygen supply tube 34 is attached to the curved portion 33a, and the oxygen can be supplied to the face. Once having come into collision with the airway case 12 and wafted, the oxygen supplied by way of the prongs 35 can be aspirated by the nostrils and the mouth 32. The orientation in which the extremities of the prongs 35 are directed toward the face can be adjusted by the angle at which the oxygen supply tube 34 is attached to the curved portion 33a of the hook 33.

Figure 10B:
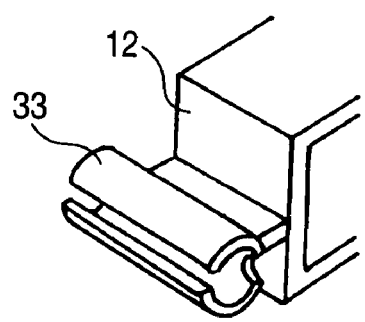
FIG. 10B is a fragmentary perspective view of a seventh modified example of the sensor of the second embodiment.

As a seventh modified example of this embodiment shown in FIG. 10B, the hook 33 may be integrally formed with the airway case 12.

The hook 33 may be attached to another side face of the airway case 12, and the hook 33 may retain the prongs 35.

There will be described a third embodiment of the invention in which a vent hole for immediately discharging a gas remaining in the airway passage 13 during the oral expiration, in order to enhance the measurement accuracy for the concentration, the partial pressure, or the presence/absence of the carbon dioxide even in a case where the amount of a respiration gas is small.

This embodiment shown in FIGS. 11 through 14 differs from the first embodiment shown in FIGS. 1 through 4 only in terms of ventilation. Therefore, the same elements are designated by the same reference numerals, and the repetitive explanations for those will be omitted.

In an upper portion of the airway case 12, the pair of inlets 21a, 21b of the flexible tube 21 having a relatively small cross-sectional area are merged with each other in the vicinity of the airway passage 13, thereby defining a merge section 40 having a relatively large cross-sectional area. The merge section 40 is in close proximity to and in communication with the airway passage 13 having a much larger cross-sectional area. The nasal expiration gas inlet member 42 is constituted of the soft tube 21 and the merge section 40. In order to immediately discharge the gas remaining in the airway passage 13 simultaneously when breath is expired from the mouth, a vent hole 41 is formed for bringing the inside of the merge section 40 into communication with the outside.

The vent hole 41 is disposed downstream of the airway passage 13 with respect to the direction of flow of the oral expiration gas. The location and shape of the vent hole 41 are determined so as not to oppose to the flow of the nasal expiration gas, in order to block leakage of the nasal expiration gas to the outside by way of the vent hole 41. Further, the location and shape of the vent hole 41 are determined such that the face does not hinder circulation of the gas passing through the vent hole 41.

Figure 11:
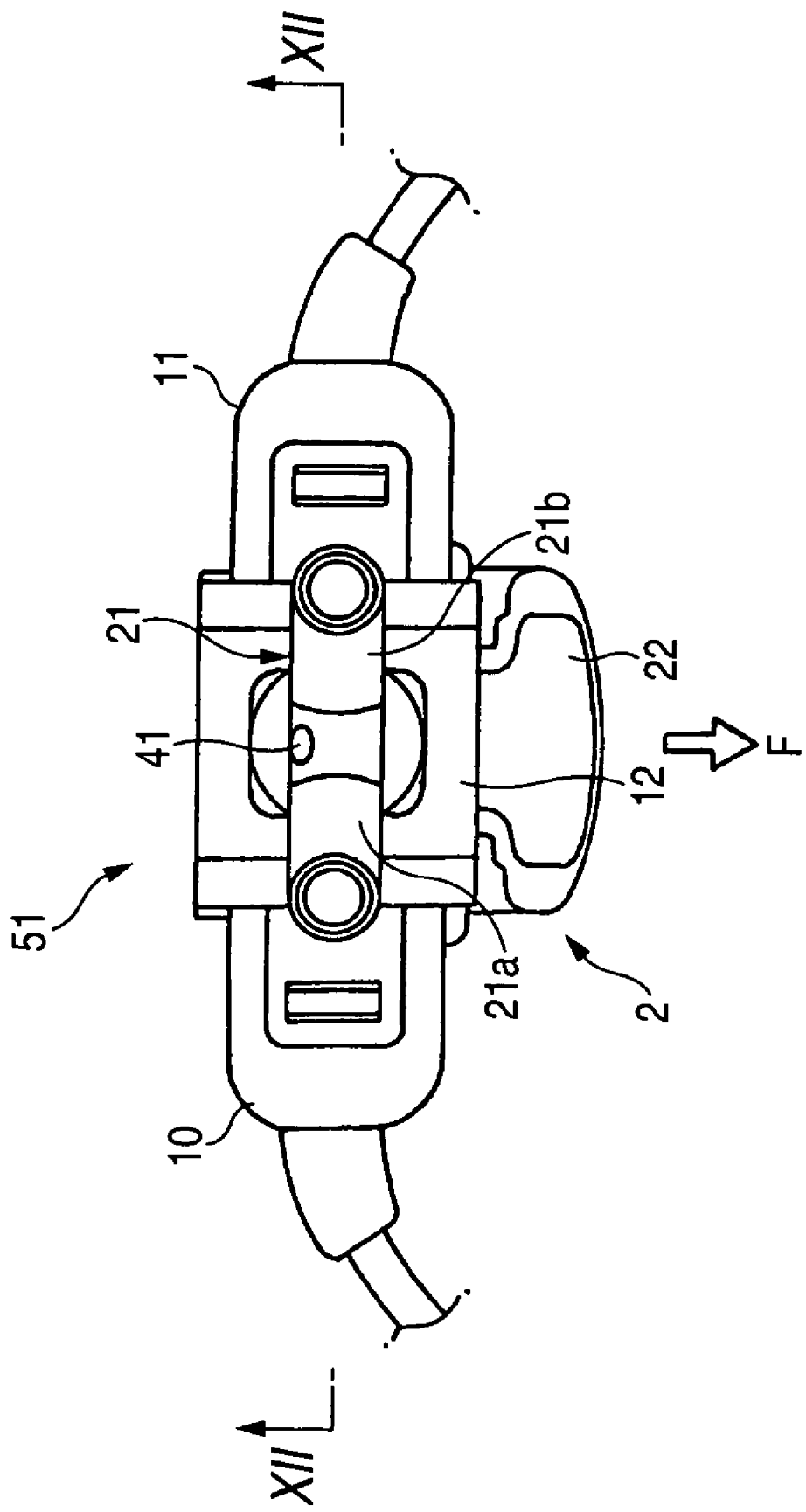
FIG. 11 is a top plan view of a carbon dioxide sensor according to a third embodiment of the invention.
Figure 12:
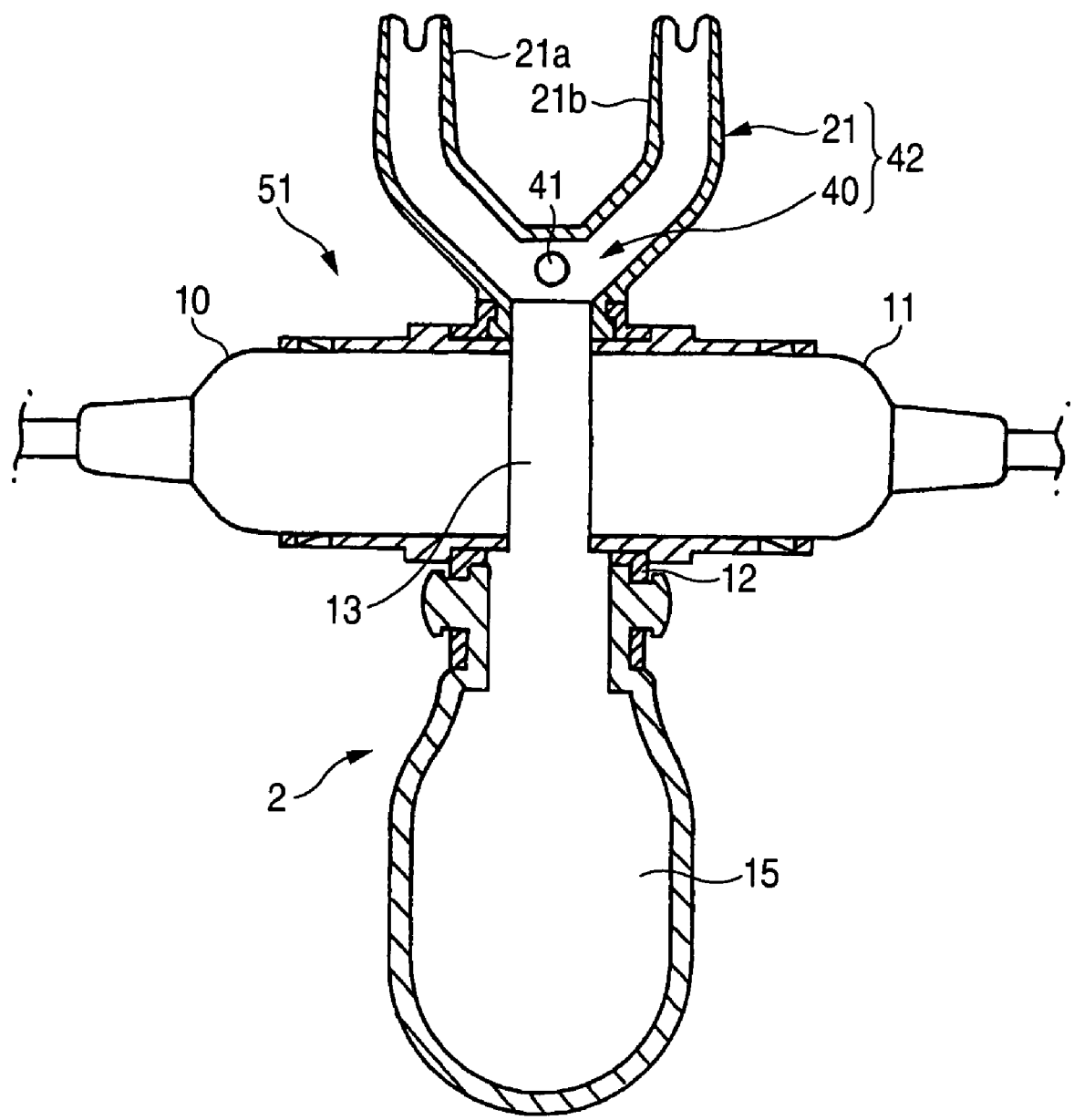
FIG. 12 is a cross-sectional view of the sensor taken along line XII-XII shown in FIG. 11.
Figure 13:
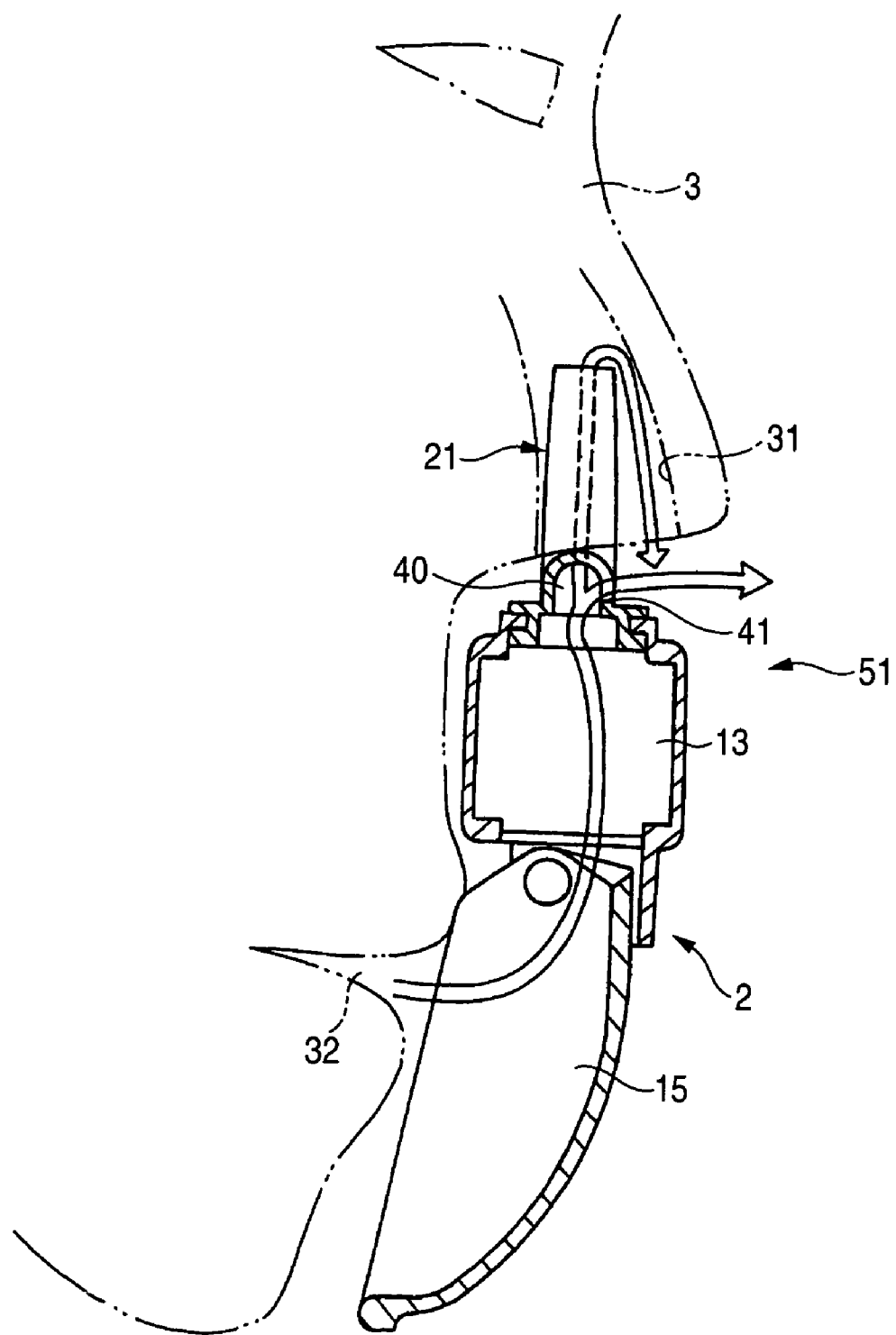
FIG. 13 is a view showing flow of an oral expiration gas when the sensor of the third embodiment is attached to the patient.

As shown in FIGS. 11 through 13, the vent hole 41 is circular (e.g., having a diameter of 2 mm) and formed in an exterior wall of the merge section 40 so as to situate at the center of the exterior wall facing away from the face. In FIG. 11, the carbon dioxide sensor 51 is attached such that the direction of arrow F faces the face of the patient 3.

As indicated by the arrow in FIG. 13, the oral expiration gas is guided to the airway passage 13 by way of the mouth guide 15. The gas remaining in the airway passage 13 is pushed to the merge section 40. The thus-pushed gas flows to the outside by way of the vent hole 41 and simultaneously enters the nostrils 31 by way of the soft tube 21, subsequently flowing outside. Since the soft tube 21 is elongated and has a relatively small cross-sectional area, the flow resistance against the gas is large. Moreover, the vent hole 41 is provided in the merge section 40 adjacent to the airway passage 13. Consequently, the gas is likely to flow outside via the vent hole 41.

Even when the soft tube 21 has been clogged with a nasal mucus, the gas can flow outside from the vent hole 41 as a result of inflow of the oral expiration gas to the airway passage 13.

As mentioned above, since the carbon dioxide sensor has the vent hole 41, excellent escape of the gas from the inside of the airway passage 13 is achieved. Therefore, when the oral expiration is performed, the gas remaining in the airway passage 13 is discharged to the outside, and the oral expiration gas immediately flows into the airway passage 13. Consequently, even when the amount of respiration is small, the concentration, partial pressure, or presence/absence of carbon dioxide in the oral expiration gas can be measured accurately.

Next will be described an experiment in which the concentration of carbon dioxide in the oral expiration gas is measured and evaluated through use of the carbon dioxide sensor having the vent hole and the carbon dioxide sensor not having any vent hole.

The measurement was evaluated by measuring the concentration of carbon dioxide through use of the carbon dioxide sensor 51 having the vent hole 41, the sensor being shown in FIGS. 11 through 13, and the carbon dioxide sensor 1 not having the vent hole 41, and by comparing the results of measurement. Measurement was performed as described below.

A model for a human face and a nostril was used. As shown in FIG. 13, the sensor was attached to the model. The amount of gas to be measured corresponding to weak expiration was delivered by a delivery pump for a given time period corresponding to a time period during which an ordinary person expires at a single breath, to thereby discharge the gas from the mouth. Subsequently, the amount of gas corresponding to weak respiration was sucked by a vacuum pump in place of the delivery pump for a given time period corresponding to a time period during which the ordinary person inspires at a single breath. These operations were performed alternately and consecutively. A gas, whose concentration is close to the concentration of carbon dioxide in an expired gas of the human attained by mixing carbon dioxide in air, was used as the gas to be measured.

Figure 14:
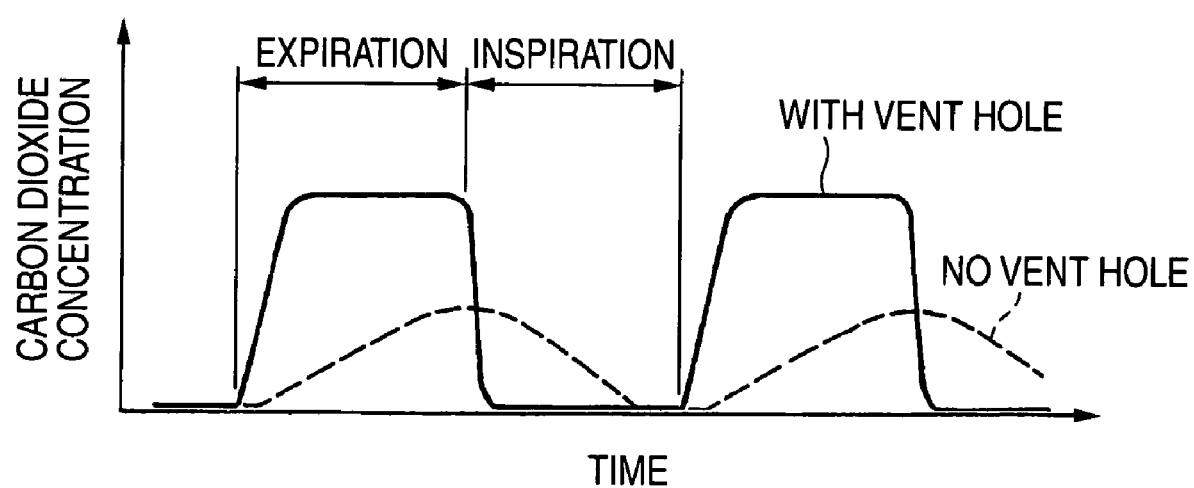
FIG. 14 is a graph for explaining an advantageous effect of the sensor of the third embodiment.

Measurement results are shown in FIG. 14. A solid line shows the results obtained by the sensor having the vent hole 41, whereas a dashed line designate the results obtained by the sensor not having the vent hole 41.

As can be seen from FIG. 14, when the vent hole 41 is formed, the concentration of carbon dioxide has increased and become saturated immediately after initiation of ejection of the gas to be measured. This shows immediate flow of the gas to be measured into the airway passage 13, and the effect of the vent hole 41 is exhibited well.

In contrast, when the vent is not formed, the concentration of carbon dioxide gradually increases with a lag even when the gas to be measured has been discharged. The increase continues until initiation of sucking action. Subsequently, the concentration of carbon dioxide does not saturate and gradually decreases. This shows that flow of the gas to be measured into the airway passage 13 is performed gradually.

As mentioned above, even when the amount of respiration is small, the concentration of carbon dioxide in the expired gas from the mouth can be measured accurately by the vent hole 41.

When the vent hole 41 is formed, the concentration of carbon dioxide has decreased rapidly after initiation of sucking operation. This shows that an external gas flows into the airway passage 13 by way of the vent hole 41 and that the gas to be measured has been immediately discharged to the outside.

The nasal expiration gas inlet member 42 has been described as being constituted of a pair of tubes (i.e., the pair of inlets 21a, 21b of the soft tube 21 to be inserted into the nostrils 31) and the merge section 40 merged with the respective ends of the tube. However, the nasal expiration gas inlet member 42 may be constituted of a single tube. In this case, a vent hole is formed in an area of the tube, where is in close proximity to a node between the tube and the airway passage 13.

The vent hole 41 is given a circular shape having a diameter of 2 mm and is formed in the exterior wall of the merge section 40 so as to be located in the center of the portion thereof facing away from the living body. The vent hole 41 may assume any shape or location, so long as the above-described requirements are satisfied.

Figure 15:
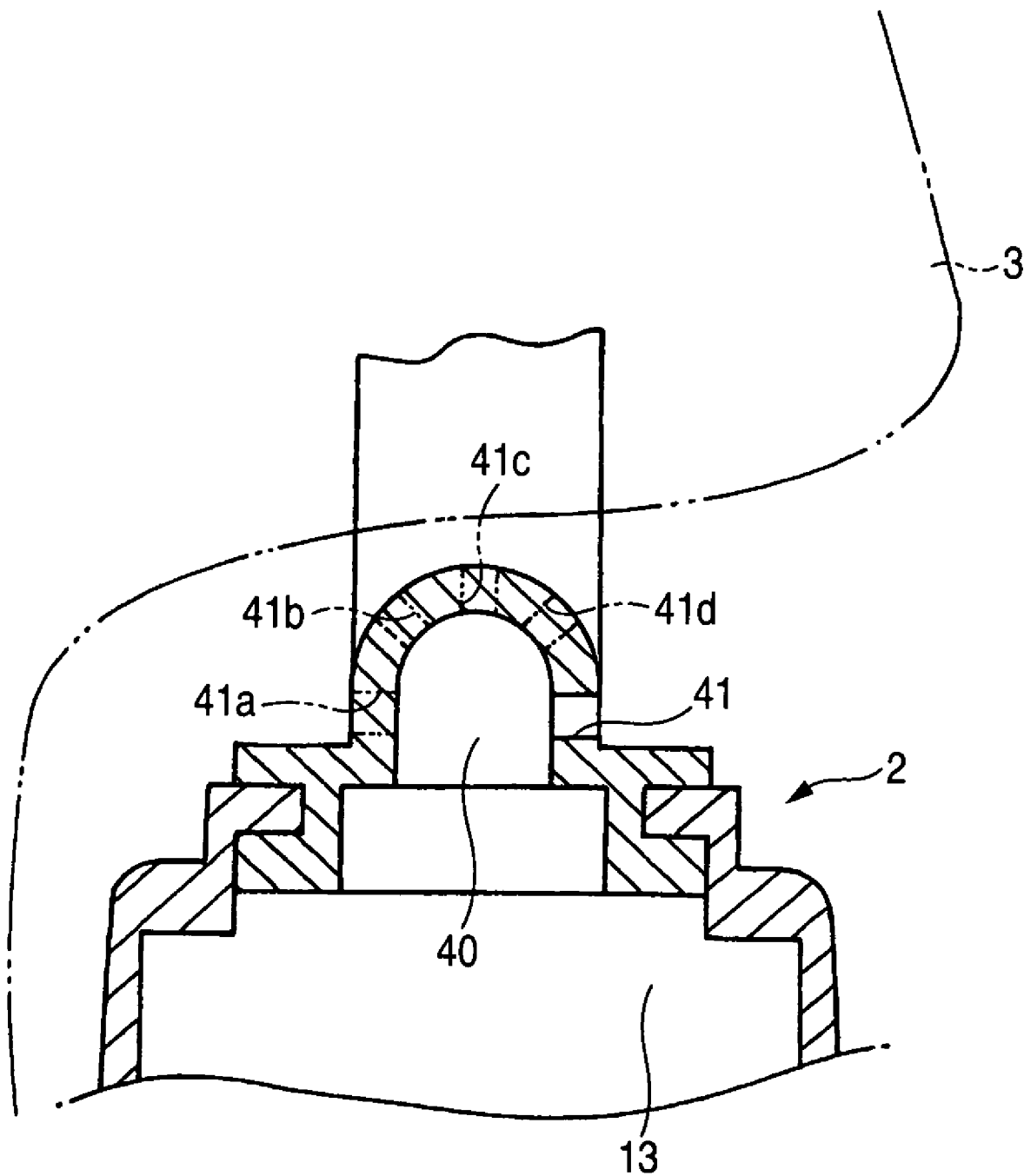
FIG. 15 is a cross-sectional view showing a modified example of the sensor of the third embodiment.
Figure 16:
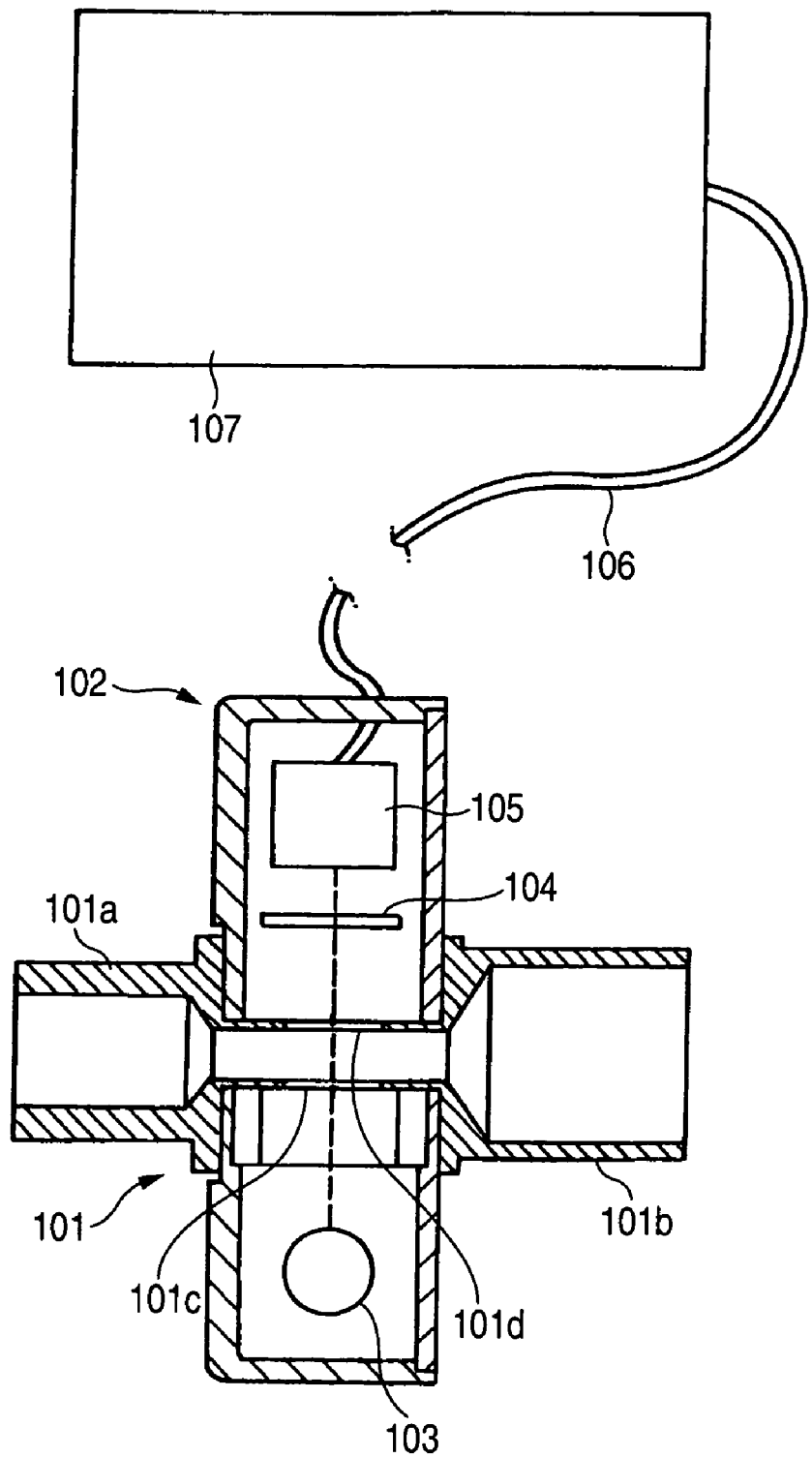
FIG. 16 is a view showing a first related-art carbon dioxide sensor.
Figure 17:
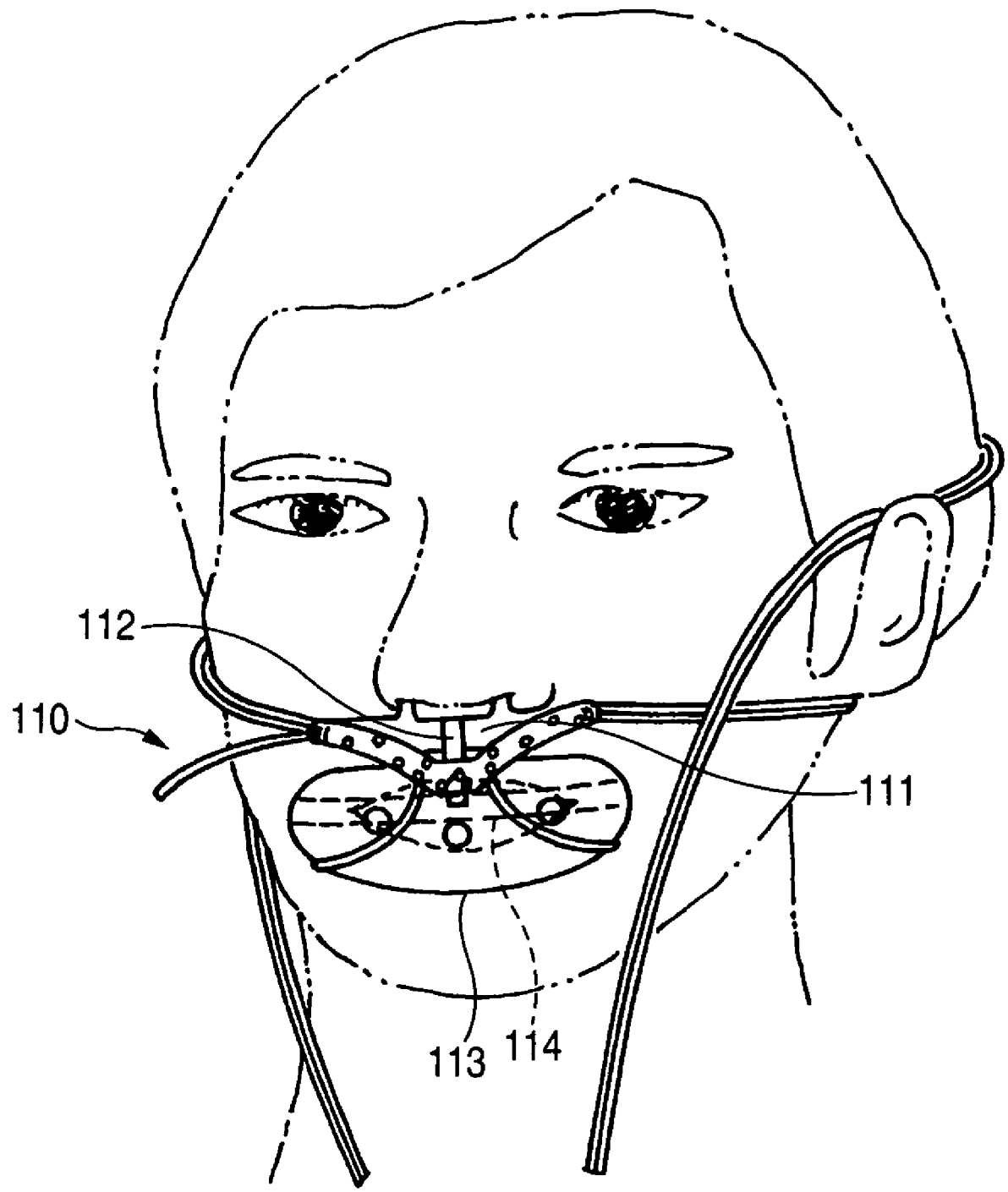
FIG. 17 is a view showing second related-art carbon dioxide sensor.

FIG. 15 shows a modified example of this embodiment featuring a different layout of the vent hole 41. As illustrated by phantom lines, the vent hole can be formed in any one of locations 41a, 41b, 41c, and 41d. In a position where the vent hole 41c or the like may be closed by the living body, an opening of the vent hole 41c may be set to an oval shape. Although the diameter of the vent hole 41 is taken as 2 mm, the diameter can be set so as to satisfy the foregoing requirements in view of the structure, such as the soft tube 21, the merge section 40, and the airway passage 13.

Although the present invention has been shown and described with reference to specific preferred embodiments, various changes and modifications will be apparent to those skilled in the art from the teachings herein. Such changes and modifications as are obvious are deemed to come within the spirit, scope and contemplation of the invention as defined in the appended claims.

What is claimed is:

1. An airway adapter of a sensor for detecting a carbon dioxide gas in an expiration gas of a living body, the airway adapter comprising:
   an airway case, adapted to be disposed below nostrils of the living body, and formed with an airway passage extending across an optical axis of a light beam emitted from a light emitter of the sensor, the airway case having a front side and a back side that opposes the front side, the back side positioned adjacent a face of the living body when the airway case is positioned on the face of the living body;
   an oxygen supply tube; and
   a retainer that retains the oxygen supply tube on the front side of the airway case such that an exit of the oxygen supply tube is adjacent a side of the airway case other than the back side of the airway case, when the back side of the airway case is adjacent the face of the living body, whereby an oxygen gas supplied from the exit of the oxygen supply tube is not directly injected into the nostrils.

2. The airway adapter as set forth in claim 1, wherein the oxygen supply tube is retained at such a position that a gap is defined between the prongs and the nostrils.

3. The airway adapter as set forth in claim 1, further comprising a mouth guide, adapted to be disposed in front of a mouth of the living body so as to define a space communicated with the airway passage, the mouth guide being pivotably supported on the airway case.

4. The airway adapter as set forth in claim 1, further comprising an inlet member, adapted to be inserted into at least one of the nostrils having a passage for guiding a nasal expiration gas to the airway passage, the inlet member being formed with a vent hole communicating the passage and an exterior of the inlet member.

5. The airway adapter as set forth in claim 4, wherein:
   the passage of the inlet member is defined by a pair of tube members adapted to be inserted into the nostrils and a junction at which the tube members are merged; and
   the vent hole is formed at the junction.

6. The airway adapter as set forth in claim 5, wherein the vent hole is arranged such that a flow of a gas discharged from the vent hole is not substantially interfered by the living body.

7. The airway adapter as set forth in claim 6, wherein the vent hole is arranged so as not to oppose to a face of the living body.

8. A sensor for detecting a carbon dioxide gas in an expiration gas of a living body, comprising:
   an oxygen supply tube;
   a photo emitter;
   a photo receiver; and
   an airway adapter, which supports the photo emitter and the photo receiver such that a light beam emitted from the photo emitter is received by the photo receiver, the airway adapter comprising:
   an airway case, adapted to be disposed below nostrils of the living body, and formed with an airway passage extending across an optical axis of the light beam, the airway case having a front side and a back side that opposes the front side, the back side positioned adjacent a face of the living body when the airway case is positioned on the face of the living body; and
   a retainer that retains the oxygen supply tube on the front side of the airway case such that an exit of the oxygen supply tube is adjacent a side of the airway case other than the back side of the airway case, when the back side of the airway case is adjacent the face of the living body, whereby oxygen gas supplied from the exit of the oxygen supply tube is not directly injected into the nostrils.

9. A sensor for detecting a carbon dioxide gas in an expiration gas of a living body, comprising:
   a photo emitter;
   a photo receiver;
   an oxygen supply tube, having prongs adapted to supply an oxygen gas therefrom to nostrils of the living body and extending in a direction not opposing the nostrils when the sensor is positioned on a face of the living body;

an airway adapter, which supports the photo emitter and the photo receiver such that a light beam emitted from the photo emitter is received by the photo receiver, the airway adapter comprising:

an airway case, adapted to be disposed below the nostrils, and formed with an airway passage extending across an optical axis of the light beam, the airway case having a front side and a back side that opposes the front side, the back side positioned adjacent a face of the living body when the airway case is positioned on the face of the living body; and a retainer that retains the oxygen supply tube on the front side of the airway case such that the prongs of the oxygen supply tube is adjacent a side of the airway case other than the back side of the airway case, when the back side of the airway case is adjacent the face of the living body, whereby an oxygen gas supplied from the prongs of the oxygen supply tube is not directly injected into the nostrils.

10. The sensor as set forth in claim 9, wherein the prongs extend along a top side of the airway case.

11. The sensor as set forth in claim 9, wherein the prongs extend along the front side of the airway case.

12. The sensor as set forth in claim 9, wherein the prongs extend along a bottom side of the airway case.

13. The sensor as set forth in claim 9, wherein the prongs oppose the photo emitter and the photo receiver.

14. The sensor as set forth in claim 1, wherein the exit of the oxygen supply tube is placed on a top side of the airway case.

15. The sensor as set forth in claim 1, wherein the exit of the oxygen supply tube is placed on a front side of the airway case.

16. The sensor as set forth in claim 1, wherein the exit of the oxygen supply tube is placed on a bottom side of the airway case.

* * * * *